Nov. 7, 1950 F. H. HOWARD Plant Pat. 986
ROSE PLANT
Filed Nov. 22, 1949
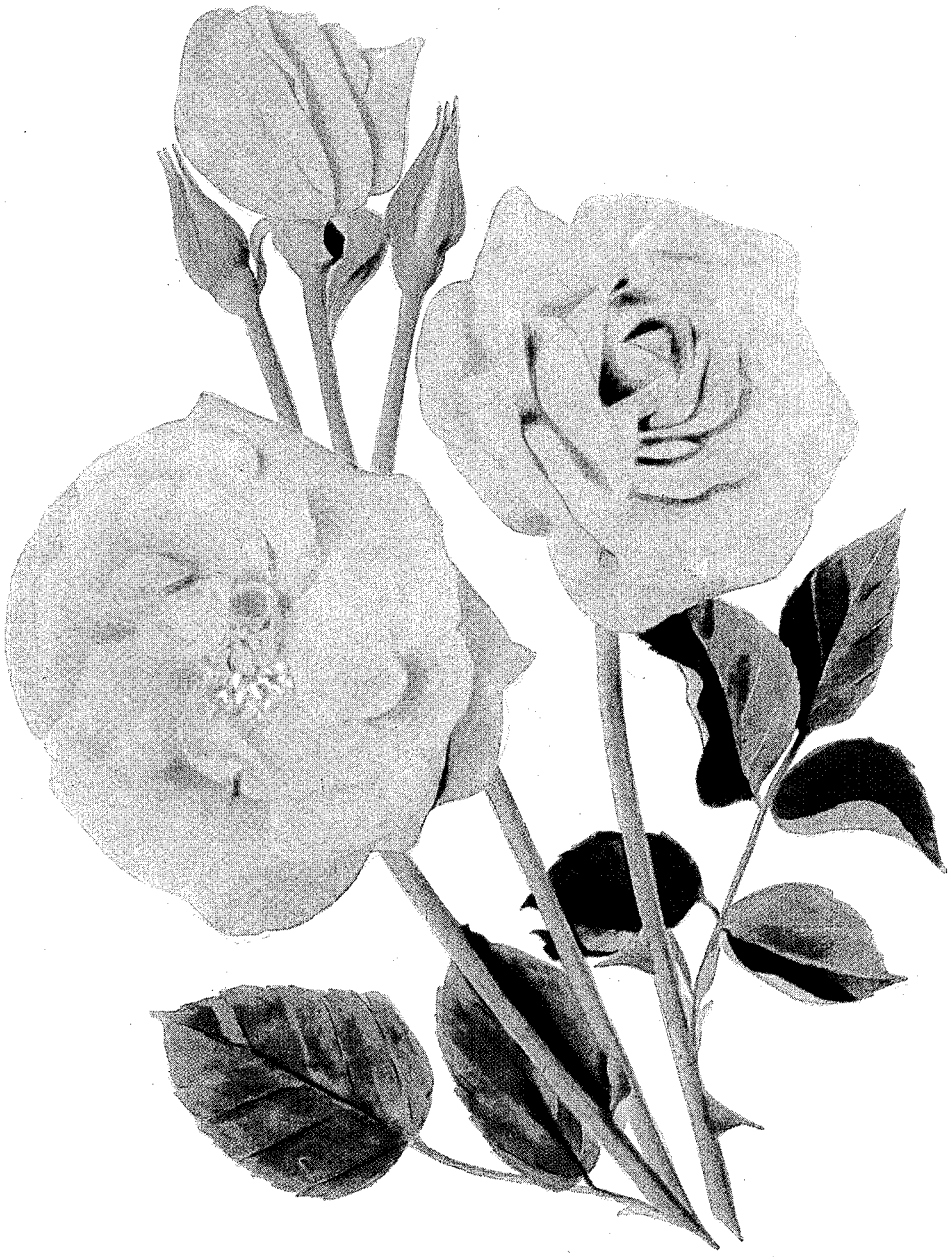
INVENTOR
Fred H. Howard, Deceased
By Minnie J. Howard, Executrix
By Orville M Kile
Plant Pat. Agt.

Patented Nov. 7, 1950

Plant Pat. 986

UNITED STATES PATENT OFFICE

986

ROSE PLANT

Fred H. Howard, deceased, late of Montebello, Calif., by Minnie J. Howard, executrix, Montebello, Calif., assignor to Howard & Smith, Montebello, Calif.

Application November 22, 1949, Serial No. 128,839

1 Claim. (Cl. 47—61)

The present invention relates to a new variety of hybrid tea rose plant which was produced in a garden at Montebello, California, as the result of a cross between the varieties Mauna Loa (unpatented) and Queen Mary (Plant Patent No. 249). Asexual reproduction of this variety in these same gardens by means of budding has shown its characteristics to be permanent.

This is one of the most fragrant of pink roses yet developed. It is very prolific in its production of flowers and sometimes four or five flowers break out in one truss. Lack of burning in very hot sun is a notable feature. Grown in the fields with many other varieties of a similar color, this variety alone showed no sign of burning on a recent morning with temperature high in the nineties.

Accompanying illustrations show three specimens of the flower of this new variety in various stages of opening, together with two small buds and portions of stems and foliage.

Following is a detailed description of this new variety of rose plant. Color plate numbers refer to Ridgway's Color Standards and Nomenclature.

*The plant*

Growth: Upright, vigorous and healthy. Attains a height of four feet at full maturity. Grows in good proportions with sufficient space between the branches to avoid crowding of limbs.

Blooming habit: Continuous and very free-blooming. Has the unusual habit of stems breaking almost up to the last eye and producing flower buds one crop following the other on the same stems. Sometimes four or five flowers break out in one truss.

Disease resistance: Variety has never been bothered with blackspot and, although some mildew occurs at times, it is much less prevalent than on similar pink varieties.

Burn resistance: No sign of burning in very hot weather has ever been observed.

Stems: Strong and sturdy. Length about 18 to 24 inches. Color olive green.

Thorns: Numerous; reddish-brown; approximately ¼ inch long; extend at right angles to stem.

Foliage:

*Quantity.*—Sufficient to fully clothe the wood.
*Leaflets.*—Three to five.
*Shape.*—Oval, with rounded or flattened base.
*Size.*—Terminal leaflet approximately 2 inches by 3 inches.
*Texture.*—Leathery and smooth.
*Appearance.*—Bright but not glossy.
*Stipules.*—Prominent and foliaceous.

*Color.*—Approximately Forest Green (Pl. XVII).

*The flower*

Bud:

*Size.*—1½ inches long.
*Shape.*—Ovoid.
*Color.*—Rose Color (Plate XII).
*Peduncle.*—Rigid; 2 to 3 inches long, bringing foliage close to flower.
*Calyx.*—Medium in size; prominent.
*Sepals.*—1½ inches long; simple; reflex early.

Bloom:

*Size.*—Average diameter 4 to 4½ inches when fully open. Sometimes larger.
*Form.*—Globular and high-centered, opening to informal revealing large stamens.
*Petalage.*—30 to 40 petals.
*Color.*—Approximately Rose Color (Pl. XII).
*Fragrance.*—Highly fragrant with usual hybrid tea fragrance. More fragrant than any other pink rose known to me.
*Longevity.*—Keeping qualities are very good.

Petals:

*Shape.*—Round to obovate; deeply cupped; edge smooth.
*Size.*—Outer petals 1½ inches by 1½ inches to 2 inches by 2 inches. Inner petals smaller.
*Aspect.*—Smooth.
*Substance.*—Heavy and waxlike.
*Behavior.*—Petals drop off cleanly.

Reproductive organs:

*Pistils.*—Numerous; light rose red. Length $\frac{3}{16}$ to ¼ inch. *Stigma* bright yellow.
*Stamens.*—Numerous; surround pistils. *Filaments* rose red; ¼ to ⅜ inch long. *Anthers* prominent; light buff to bright yellow.
*Receptacle.*—Prominent, with rose red disc or ring.

What is claimed is:

The new and improved variety of hybrid tea rose plant, substantially as herein shown and described, characterized particularly by its vigorous, well-proportioned growth; its resistance to burning in hot sun; its habit of breaking to the last eye thus enabling it to become a very prolific bloomer; its occasional truss formation of four or five flowers; and its rose colored flowers with heavy waxlike petals and abundant fragrance.

MINNIE J. HOWARD,
*Executrix of the Last Will and Testament of Fred H. Howard, Deceased.*

No references cited.